US012710555B2

(12) United States Patent
Li et al.

(10) Patent No.: US 12,710,555 B2
(45) Date of Patent: Aug. 18, 2026

(54) SYSTEM AND METHOD FOR IMAGE RECONSTRUCTION IN POSITRON EMISSION TOMOGRAPHY

(71) Applicant: SHANGHAI UNITED IMAGING HEALTHCARE CO., LTD., Shanghai (CN)

(72) Inventors: Hongdi Li, Houston, TX (US); Yun Dong, Shanghai (CN); Yang Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 482 days.

(21) Appl. No.: 18/340,880

(22) Filed: Jun. 25, 2023

(65) Prior Publication Data

US 2023/0333269 A1 Oct. 19, 2023

Related U.S. Application Data

(63) Continuation of application No. 17/452,087, filed on Oct. 25, 2021, now Pat. No. 11,686,867, which is a
(Continued)

(51) Int. Cl.
*G01T 1/29* (2006.01)
*A61B 6/00* (2024.01)
*A61B 6/03* (2006.01)

(52) U.S. Cl.
CPC ............ *G01T 1/2985* (2013.01); *A61B 6/037* (2013.01); *A61B 6/5211* (2013.01)

(58) Field of Classification Search
None
See application file for complete search history.

(56) References Cited

U.S. PATENT DOCUMENTS 4,415,807 A * 11/1983 Friauf .................. G01T 1/2985 250/369
5,210,420 A 5/1993 Hartz et al.
(Continued)

FOREIGN PATENT DOCUMENTS

| | | |
|---|---|---|
| CN | 102813527 | 12/2012 |
| CN | 103099637 A | 5/2013 |

(Continued)

OTHER PUBLICATIONS

International Search Report in PCT/CN2016/085434 mailed on Jan. 26, 2017, 6 pages.

(Continued)

*Primary Examiner* — Edwin C Gunberg
(74) *Attorney, Agent, or Firm* — METIS IP LLC

(57) ABSTRACT

The present disclosure provides a positron emission tomography (PET) system and an image reconstruction method thereof. The PET system may include a plurality of detector units arranged along an axial direction, each detector unit of the plurality of detector units being configured to generate a plurality of single event counts; a plurality of coincidence logic circuits, each coincidence logic circuit of the plurality of coincidence logic circuits being operably connected to at least one of the plurality of detector units; and a computing system configured to reconstruct an image by performing, based on a plurality of coincidence counts generated by the plurality of coincidence logic circuits, forward projection calculation and backward projection calculation.

20 Claims, 12 Drawing Sheets

Related U.S. Application Data continuation of application No. 16/945,955, filed on Aug. 3, 2020, now Pat. No. 11,156,732, which is a continuation of application No. 15/609,263, filed on May 31, 2017, now Pat. No. 10,732,305, which is a continuation of application No. PCT/CN2016/085434, filed on Jun. 12, 2016.

(56) References Cited

U.S. PATENT DOCUMENTS

| | | | | |
|---|---|---|---|---|
| 7,498,581 | B2 | 3/2009 | Wang et al. | |
| 10,732,305 | B2 | 8/2020 | Li et al. | |
| 11,156,732 | B2 * | 10/2021 | Li | A61B 6/037 |
| 11,686,687 | B2 * | 6/2023 | Haught | G01N 33/28 356/237.1 |
| 2004/0097800 | A1 | 5/2004 | Crosetto | |
| 2004/0195512 | A1 | 10/2004 | Crosetto | |
| 2008/0095300 | A1 * | 4/2008 | Zingelewicz | G01N 23/04 378/4 |
| 2008/0317194 | A1 | 12/2008 | Gagnon et al. | |
| 2011/0301918 | A1 | 12/2011 | Haselman et al. | |
| 2011/0309256 | A1 | 12/2011 | Moriyasu et al. | |
| 2012/0001077 | A1 | 1/2012 | Inoue et al. | |
| 2012/0126125 | A1 | 5/2012 | Akazawa et al. | |
| 2016/0048615 | A1 | 2/2016 | Kolthammer et al. | |

FOREIGN PATENT DOCUMENTS

| | | | |
|---|---|---|---|
| CN | 104224219 | | 12/2014 |
| CN | 104408756 | A | 3/2015 |
| CN | 104408763 | | 3/2015 |
| CN | 105125231 | A | 12/2015 |
| CN | 109658473 | A | 4/2019 |
| CN | 108447553 | B | 7/2021 |
| JP | S63193086 | A | 8/1988 |
| WO | 2015162580 | A1 | 10/2015 |

OTHER PUBLICATIONS

Written Opinion in PCT/CN2016/085434 mailed on Jan. 26, 2017, 7 pages.

William C. J. Hunter el al., Parametric Design Study of a Long Axial Field-of-View PET Scanner using a Block-Detector Tomograph Simulation of a Cylindrical Phantom, 2009 IEEE Nuclear Science Symposium Conference Record, 3900-3903, 2009.

The Extended European Search Report in European Application No. 17882275.5 mailed on May 29, 2019, 9 pages.

* cited by examiner

SYSTEM AND METHOD FOR IMAGE RECONSTRUCTION IN POSITRON EMISSION TOMOGRAPHY

CROSS-REFERENCE TO RELATED APPLICATIONS

This application is a continuation of U.S. application Ser. No. 17/452,087 filed on Oct. 25, 2021, which is a continuation of U.S. application Ser. No. 16/945,955 (issued as U.S. Pat. No. 11,156,732) filed on Aug. 3, 2020, which is a continuation of U.S. application Ser. No. 15/609,263 (issued as U.S. Pat. No. 10,732,305) filed on May 31, 2017, which is a continuation of International Application No. PCT/CN2016/085434, filed on Jun. 12, 2016, which designates the United States of America, the entire contents of each of which are hereby incorporated by reference.

TECHNICAL FIELD

This present disclosure relates to a medical image diagnostic device, and in particular, to a system and method for image reconstruction in positron emission tomography (PET).

BACKGROUND

PET is a relatively advanced clinical imaging technique in the field of nuclear medicine. It plays an important role in medical research and clinical diagnosis.

PET is a diagnostic technique that is used to observe functions and metabolism of human organs and tissues at the molecular level. For PET, a positron radioactive drug (e.g., $^{18}$F-FDG) will be injected into a human body. Because the metabolism of fludeoxyglucose (FDG) is similar to glucose, the FDG will gather in cells that digest the glucose. The uptake of the radioactive drug by rapidly growing tumor tissues is different. A positron emitted by the decay of $^{18}$F and an electron in tissues will undergo an annihilation reaction to generate two γ photons with the same energy in opposite directions. A detector array surrounding the human body will detect the two photons using a coincidence measurement technique, and determine position information of the positron. A tomography image of positrons in the human body can then be constructed by processing the position information using an image reconstruction software.

FIG. 1 is a conventional structure of a PET system. As shown in FIG. 1, a gantry 11 includes a channel 12. An examination table 13 can move into or out of the channel 12. A patient to be examined can lie on a table surface 14 of the examination table 13. When the examination table 13 moves into the channel 12, a detector array around the channel 12 arranged in the gantry 11 can detect photons generated during the reaction.

A length of an axial field of view (FOV) of the present PET system is limited to about 25 centimeters that is much shorter than the length of a human body, e.g., 2 meters. In order to improve the PET system, there has been a plurality of PET detector units set along the axial direction of the gantry to expand the FOV in the axial direction of a body. For example, when the FOV in the axial direction of the body is expanded to about 2 meters, the whole body from the head to toes of the patient can be diagnosed simultaneously.

Expanding the FOV may enhance a sensitivity by dozens of times, but this may lead to a high counting rate that cannot be processed by a current electronic logic. Meanwhile, the speed of image reconstruction using a traditional PET technique is slowed down by dozens of times because of the high counting rate.

SUMMARY

The technical problem to be solved by the present disclosure is to provide a system and method for image reconstruction in PET, which may efficiently receive massive coincidence signals with a high counting rate.

To solve the technique problem, in one aspect of the present disclosure, a PET system is provided. The PET system may include a plurality of annular detector units arranged along an axial direction, wherein each of the detector units may generate a plurality of single event counts; and a plurality of coincidence logic circuits connected to one or more of the detector units, wherein the coincidence logic circuits may be configured to count coincidence events, wherein single event data generated by each of the detector units may be transmitted to the corresponding coincidence logic circuit, and the plurality of coincidence logic circuits may generate coincidence counts relating to the plurality of detector units in parallel.

In some embodiments, the single event data generated by the plurality of detector units may be evenly distributed to each of the coincidence logic circuits for coincidence counting.

In some embodiments, the single event data generated by the plurality of detector units may be unevenly distributed to each of the coincidence logic circuits for coincidence counting.

In some embodiments, at least part of the coincidence logic circuits may perform coincidence counting for single event data from the same detector unit.

In some embodiments, at least part of the coincidence logic circuits may perform coincidence counting for single event data from different detector units.

In some embodiments, the number of coincidence logic circuits may be equal to the number of the detector units in the PET system.

In some embodiments, each of the coincidence logic circuits may be provided on a corresponding detector unit.

In some embodiments, the number of coincidence logic circuits may be fewer than the number of the detector units in the PET system.

In some embodiments, each of the coincidence logic circuits may be connected to one or more of the detector units through a data bus.

In some embodiments, the PET system further may include a first processor. The first processor may be connected to the plurality of coincidence logic circuits, wherein coincidence counts generated by each of the coincidence logic circuit may be transmitted to the first processor. The first processor performs backward projection of the coincidence counts. The PET system performs forward projection based on the backward projection.

In some embodiments, the PET system may further include a plurality of first processors. Each of the first processors may be connected to one or more of the coincidence logic circuits. The coincidence counts generated by each of the coincidence logic circuits may be transmitted to each of the first processors. The plurality of first processors synchronically perform backward projection of the coincidence counts.

In some embodiments, the coincidence counts generated by each of the coincidence logic circuits may be transmitted to each of the first processors randomly.

In some embodiments, the plurality of first processors may be provided in one or more general-purpose computers.

In some embodiments, the PET system may further include a second processor. The second processor may be connected to the plurality of first processors. A result of backward projection generated by each of the first processors may be transmitted to the second processor. The second processor superimposes the results of backward projection. The PET system performs a forward projection based on the superimposed result of backward projection.

In another aspect of the present disclosure, a method for image reconstruction in a PET system is provided. The method may include: generating, by each of a plurality of detector units arranged along an axial direction, a plurality of single event counts; transmitting single event data generated by each of the detector units to one or more coincidence logic circuits, wherein the plurality of coincidence logic circuits may be connected to one or more of the plurality of detector units; and synchronically generating coincidence counts relating to the plurality of detector units.

In some embodiments, the single event data generated by the one or more detector units may be evenly distributed to each of the coincidence logic circuits for coincidence counting.

In some embodiments, the single event data generated by the one or more detector units may be unevenly distributed to each of the coincidence logic circuits for coincidence counting.

In some embodiments, the method may further include transmitting coincidence counts generated by each of the coincidence logic circuit to a first processor; performing, by the first processor, backward projection of the coincidence counts; and performing, by the PET system, forward projection based on the backward projection.

In some embodiments, the method may further include transmitting coincidence counts generated by each of the coincidence logic circuits to a plurality of first processors; and synchronically performing, by the plurality of first processors, backward projection of the coincidence counts.

In some embodiments, the coincidence counts generated by each of the coincidence logic circuits may be transmitted to the plurality of first processors randomly.

In some embodiments, the method may further include transmitting a result of backward projection generated by each of the first processors to a second processor; superimposing, by the second processor, the results of the backward projection; and performing, by the PET system, forward projection based on the superimposed result of the backward projection.

In another aspect of the present disclosure, a PET system is provided. The PET system may include a plurality of annular detector units arranged along an axial direction. The detector units may be configured to count single events. The PET system may further include a plurality of coincidence logic circuits that may be connected to one or more of the detector units. The coincidence logic circuits may be configured to count coincidence events. The coincidence events may include coincidence events acquired by a single detector unit or coincidence events acquired by two detector units according with a pairing rule. The system may further include a computing device. The computing device may include one or more computing nodes. The computing device may be configured to receive coincidence event counts randomly and reconstruct an image.

In some embodiments, the pairing rule may refer to numbering the plurality of detector units in a sequential order, wherein the Nth detector unit may only match detector units associated with numbers that are subsequent to N, wherein N is less than K, wherein K is the total number of the detector units, and wherein N and K are natural numbers.

In some embodiments, the PET system may include K annular detector units. The K annular detector units may include a plurality of detector pairs. Each of the detector pairs may include one or two detector units. The plurality of coincidence logic circuits may be configured to count coincidence events acquired by the detector pairs, wherein K is the total number of the detector units and K is a natural number.

In some embodiments, $K(K+1)/2$ detector pairs or less than $K(K+1)/2$ detector pairs may be selected from the plurality of detector pairs. The plurality of coincidence logic circuits may be configured to count coincidence events acquired by the selected detector pairs.

Compared with the prior art, the PET system and image reconstruction method may solve the problems of expanding the axial FOV, high counting rate of the PET detector unit and receiving massive coincidence signals by using a distributed coincidence logic circuit. As a result, the PET system with an expansive axial scanning field may achieve high sensitivity and fast imaging performance.

BRIEF DESCRIPTION OF THE DRAWINGS

Features and performance of the present disclosure are described in accordance with the embodiments below and with reference to the drawings.

FIG. 8 is a schematic diagram of an exemplary assignment of a coincidence logic task according to some embodiments of the present disclosure;

DETAILED DESCRIPTION

In the following detailed description, numerous specific details are set forth by way of example in order to provide a thorough understanding of the relevant disclosure. However, the present disclosure may be implemented in other ways different from the way described herein, and is not limited to specific embodiments described below.

Figure 1:
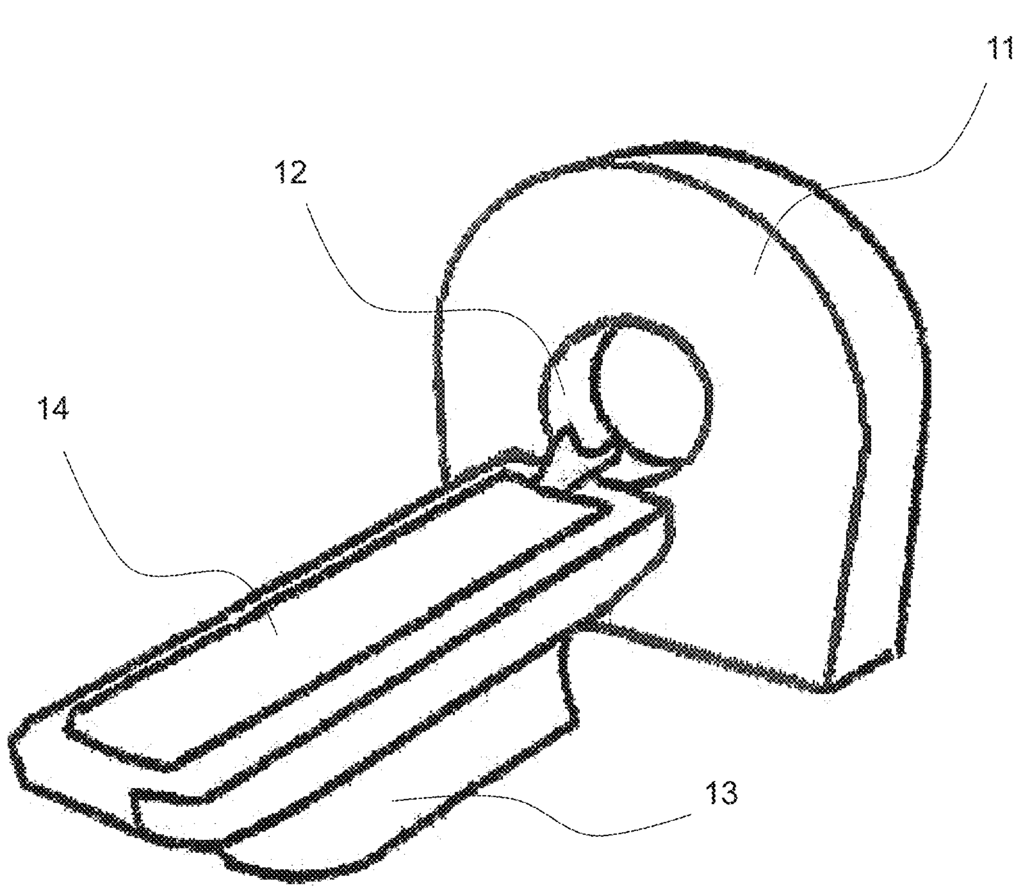
FIG. 1 is a conventional structure of a PET system.
Figure 2:
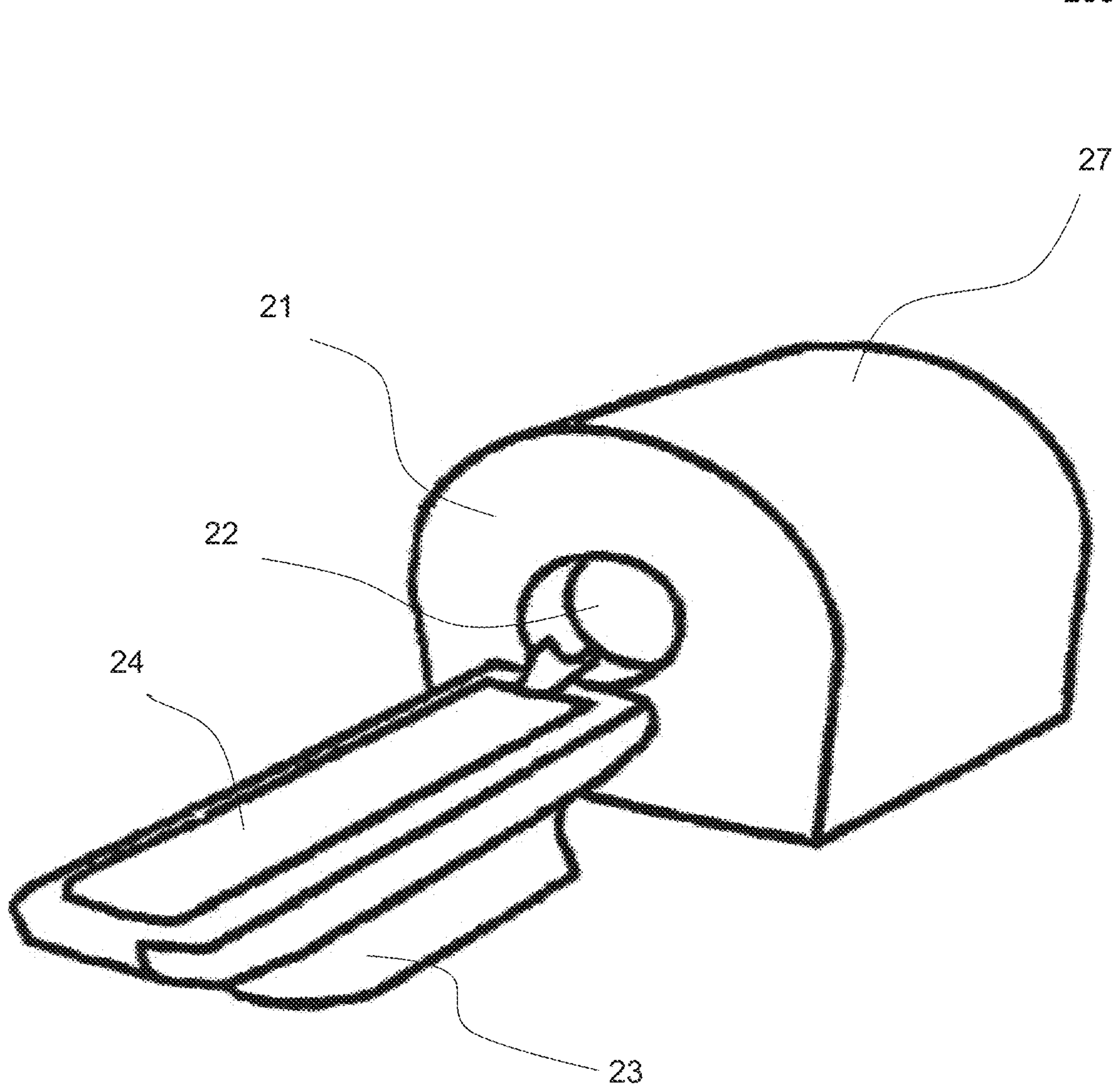
FIG. 2 is a stereogram of an exemplary PET system according to some embodiments of the present disclosure.

FIG. 2 is a stereogram of an exemplary PET system according to some embodiments of the present disclosure. As shown in FIG. 2, a gantry 21 in a PET system may include a channel 22. An examination table 23 may move into or out of channel 22. A body to be examined (also referred to herein as a "target body") can lie on a table surface 24 of the examination table 23. When the examination table 23 is moved into the channel 22, a detector array in the gantry that is arranged around channel 22 may detect γ photons. The detector array may be covered by a shell 27.

Figure 3:
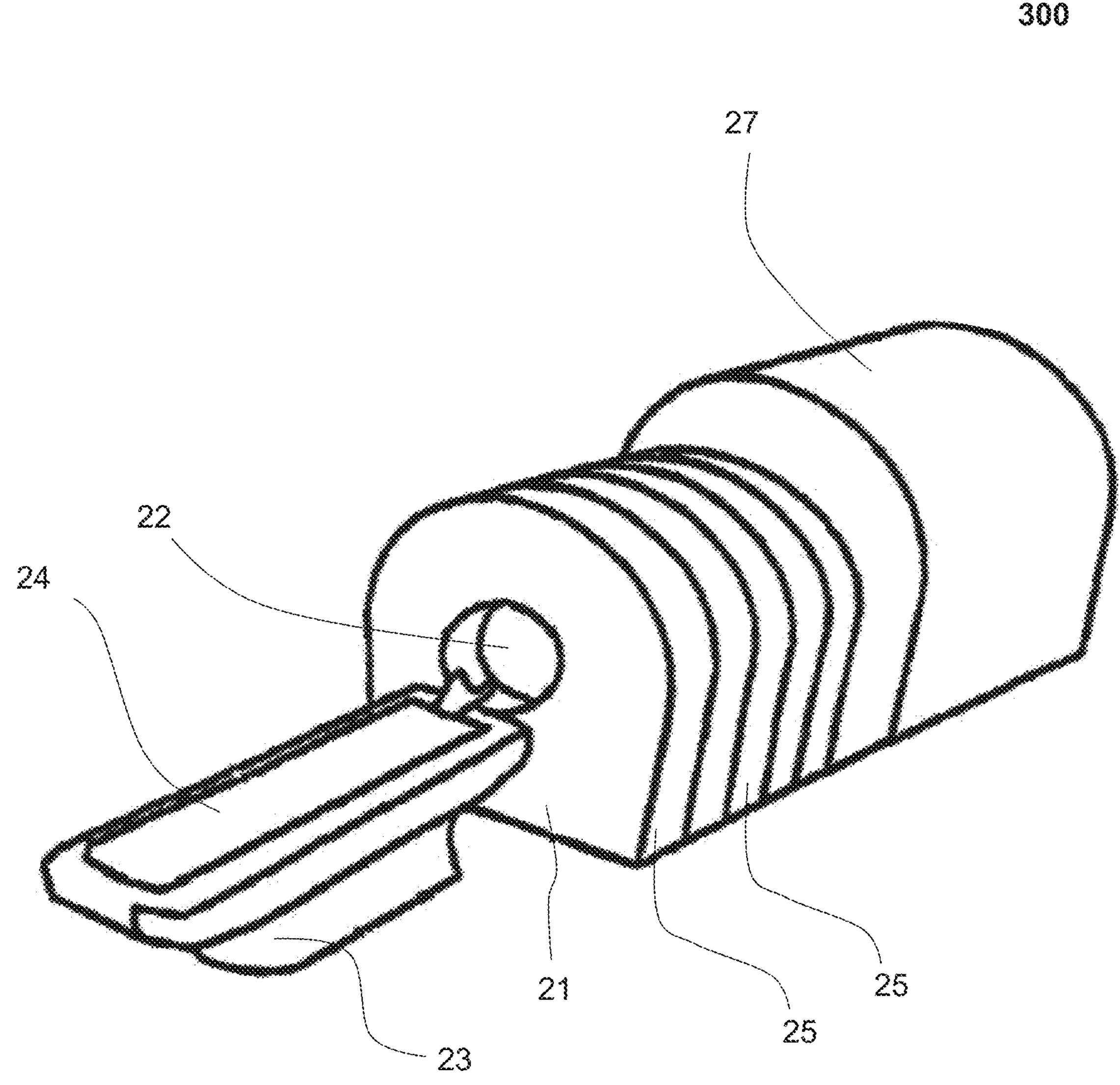
FIG. 3 is a stereogram of an exemplary PET system in which a gantry shell is removed according to FIG. 1.
Figure 4:
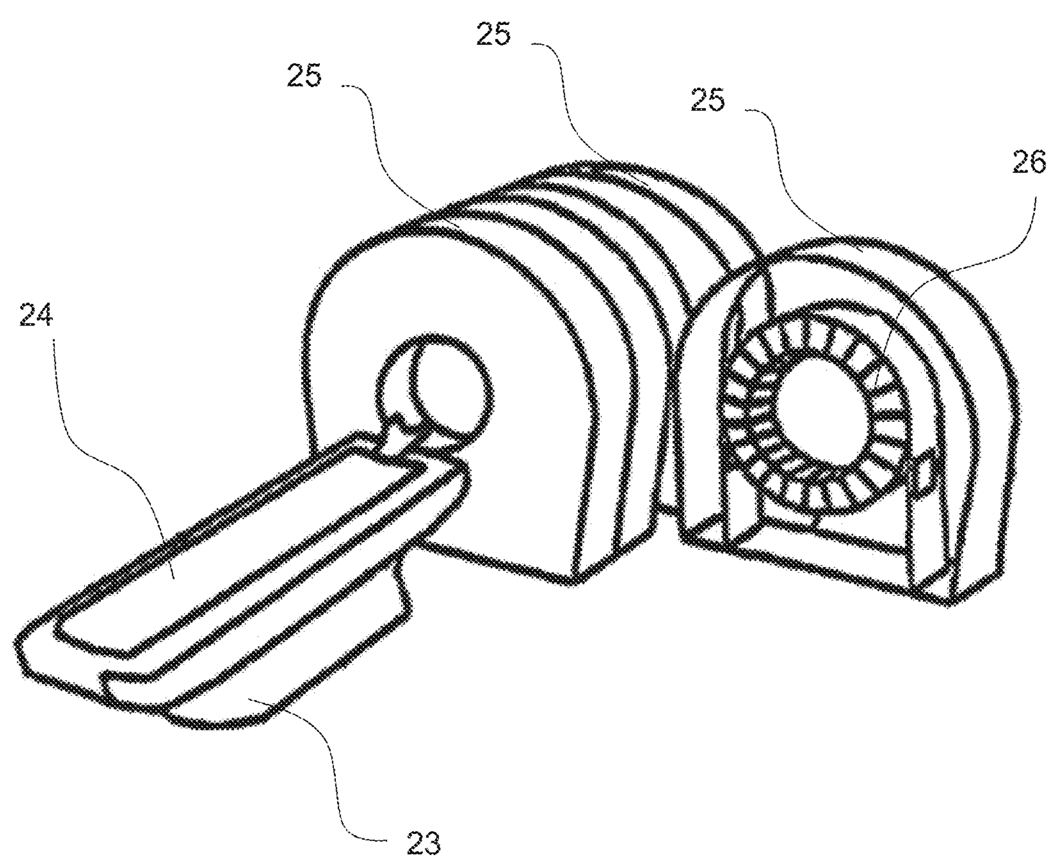
FIG. 4 is a schematic diagram of an exemplary PET system in which a detector unit is removed according to FIG. 2.

Referring FIG. 2 through FIG. 4, the gantry 21 may extend along an axial direction of a body and the detector unit 25 is arranged for the entire length of the gantry. Therefore, an FOV in the axial direction of the target body is expanded greatly. For example, when the FOV in the axial direction of the target body is extended to a length of about 100 cm, an entire trunk of the target body may be diagnosed simultaneously. The FOV in the axial direction may also be expanded to a length of about 200 cm, so that the entire body may be diagnosed simultaneously from head to toes.

In some embodiments, the PET system may include a plurality of detector units 25 arranged along the axial direction. Each of the detector units may generate a plurality of single event counts. The detector unit 25 may include a detecting component 26 and a signal processing circuit (not shown in the figures). In the detector unit 25, a plurality of detecting elements 26 may be arranged in the following way: the detecting component 26 is arranged along a circumferential direction and an axial direction of the detector unit 25.

The detecting component 26 may include, for example, a scintillation crystal and a photomultiplier. The scintillation crystal may receive a pair of annihilation γ rays of a radioactive isotope in the target body to produce visible light. Each of the scintillation crystals may be arranged so that a direction along a long axis of the scintillation crystal may be approximately consistent with a radial direction of the detector unit. The photomultiplier may be arranged on one end of the scintillation crystal that is related to the radial direction. The radial direction is orthogonal to a central axis. Typically, a plurality of scintillation crystals and a plurality of photomultipliers of the detector unit may be arranged in two concentric cylinders. The light produced by the scintillation crystal may travel toward the photomultiplier in the scintillation crystal. The photomultiplier may generate a pulse electrical signal corresponding to the amount of the light. The generated electrical signal may be provided to one or more signal processing circuits 28 shown in FIG. 5.

Figure 5:
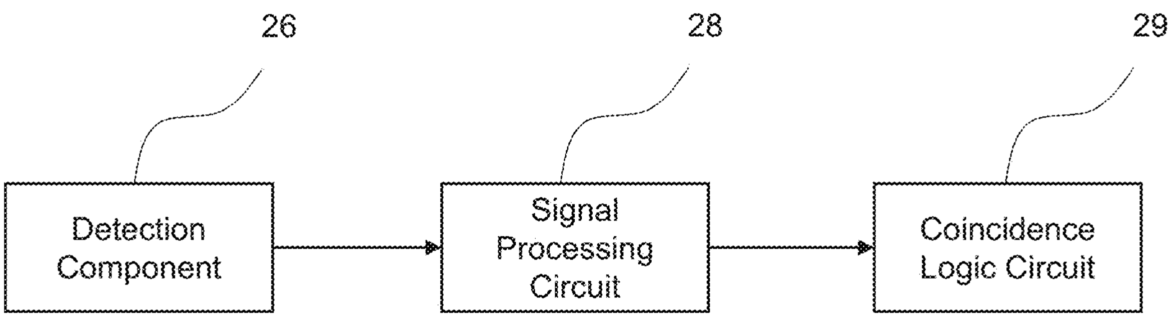
FIG. 5 is a block diagram of the PET system according to FIG. 2.

FIG. 5 is a block diagram of the PET system shown in FIG. 2. As shown in FIG. 5, the signal processing circuit 28 may generate single event data based on the electrical signal from the photomultiplier. More particularly, for example, the signal processing circuit 28 may perform operations including detection time measurement, position calculation, or energy calculation. The signal processing circuit 28 may measure detection time of γ ray of detectors during detection time measurement. More particularly, for example, the signal processing circuit 28 may monitor a peak of the electrical signal from the photomultiplier. Then the signal processing circuit 28 may detect the time when a peak value of the electrical signal exceeds a predetermined threshold value as the detection time. For example, the signal processing circuit 28 may detect the γ rays of annihilation by detecting the time when an intensity of the electric signal exceeds the threshold value. To perform the position calculation, the signal processing circuit 28 may calculate an incident position of the γ ray according to the electrical signal from the photomultiplier. The incident position of the γ ray may correspond to a position coordinate of the scintillation crystal on which the γ ray projects. To perform the energy calculation, the signal processing circuit 28 may calculate an energy value of the γ ray projected on the scintillation crystal according to the electrical signal from the photomultiplier. The generated single event data may be transmitted to one or more coincidence logic circuits 29. The coincidence circuit 29 may perform a coincidence counting operation for the single event data related to a plurality of single events.

The coincidence logic circuit 29 may repeatedly determine single event data that is related to two single events in a pair in a predetermined time period from repeated supply of single event data. In some embodiments, the predetermined time period may be from 6 nanoseconds to 18 nanoseconds. The pair of single events may be determined to be a pair of annihilation γ rays generated from the same annihilation point. The pair of single events may generally be referred to as a coincidence event. A line connecting a pair of detecting components which may detect the pair of annihilation γ rays is called as a line of response (LOR). In this way, the coincidence logic circuit may count coincidence events for each LOR.

Figure 6:
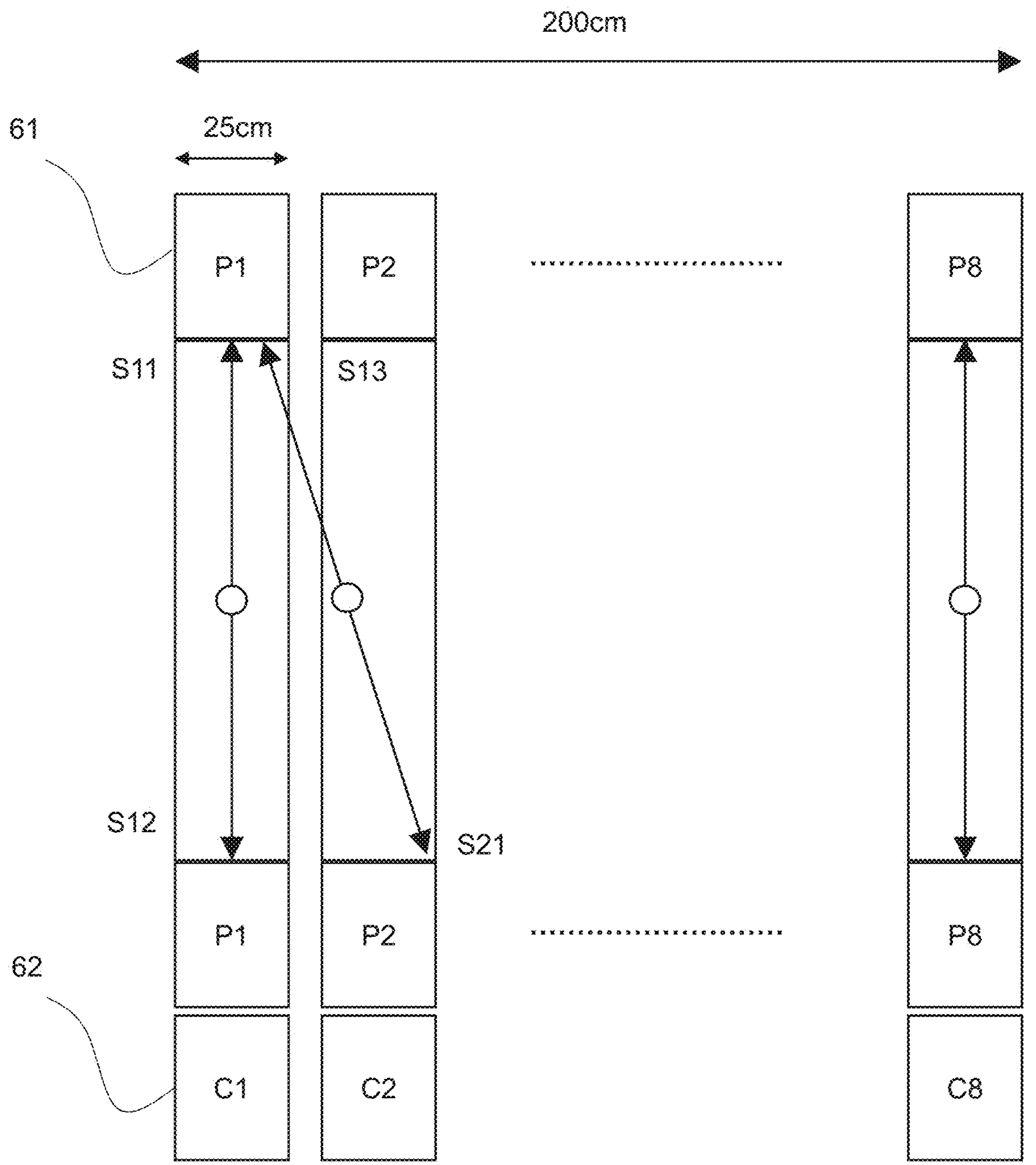
FIG. 6 is a schematic diagram of an exemplary coincidence measurement device according to some embodiments of the present disclosure.

FIG. 6 is a schematic diagram of an exemplary coincidence measurement device according to some embodiments of the present disclosure. As shown in FIG. 6, the PET system may include a plurality of detector units 61 arranged along the axial direction of the target body. For example, 8 detector units 61 arranged along the axial direction of the target body are combined into a PET system. Each detector unit 61 has an axial FOV with a length of 25 centimeters, and the combined PET system may have an axial FOV with a length of 200 centimeters.

Figure 7:
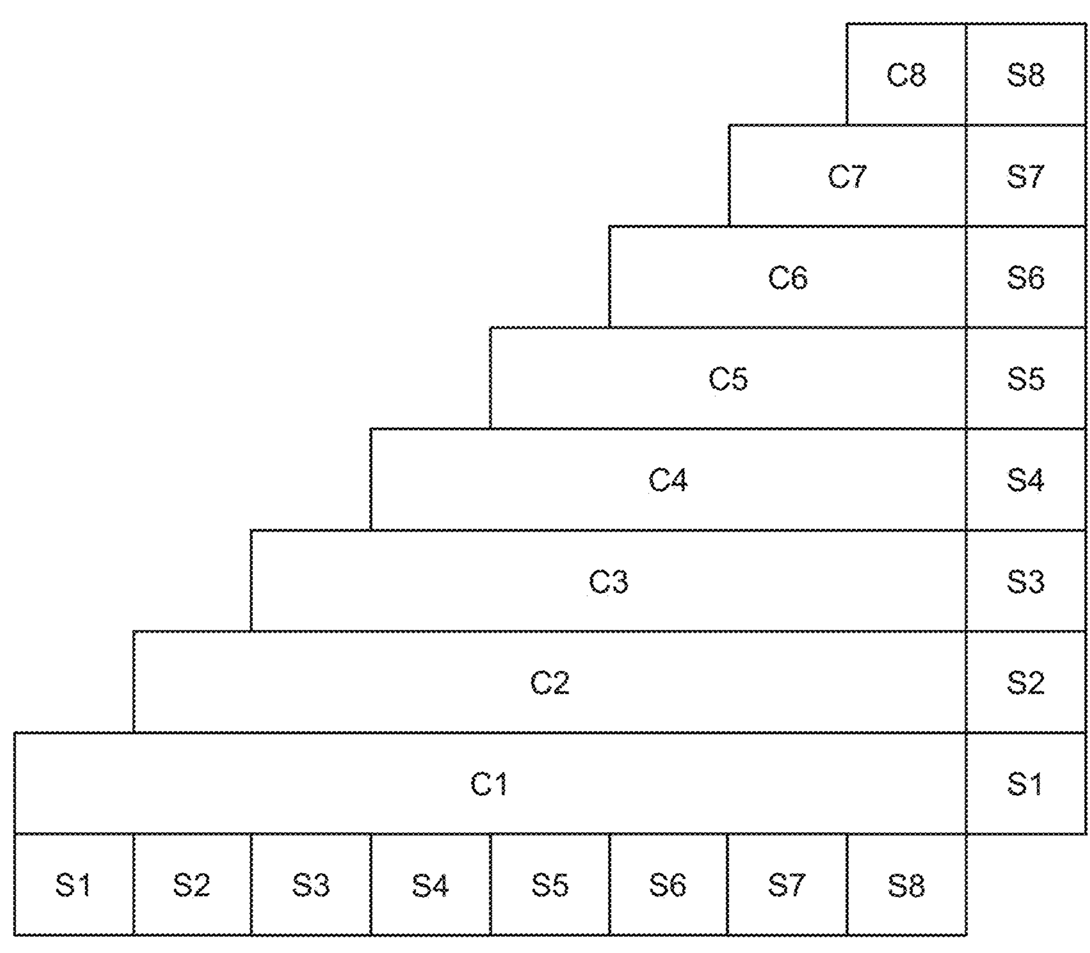
FIG. 7 is a schematic diagram of an exemplary distribution of a coincidence logic circuit according to some embodiments of the present disclosure.

Each detector unit 61 may generate a plurality of single event counts. In the present disclosure, the PET system with 8 detector units is illustrated as an example. Each detector unit is represented by $p_k$, wherein k=1, 2 . . . 8. The PET system is represented by P. A single event count (or signal) acquired by $p_k$ is represented by $S_k$. The PET system may also include a plurality of coincidence logic circuits 62. Assume that there are 8 coincidence logic circuits and each of the coincidence logic circuits is represented by $C_i$, wherein i=1, 2, . . . , 8. Each of the coincidence logic circuits 62 may be independently arranged on one detector unit 61. Each of the coincidence logic circuits 62 may connect to one or more corresponding detector units 61. The single event data generated by each of the detector units 61 may be transmitted to the corresponding coincidence logic circuit 62. The plurality of coincidence logical circuits 62 may be configured to perform coincidence counting for the single event data generated by the detector unit(s) 61. For example, when the coincidence logic circuit $C_1$ requires to use the single event data of detector unit $p_1$, $p_2$, $p_3$, and/or $p_4$, $C_1$ may connect these detector units. Similarly, the coincidence logic circuits $C_1$, $C_2$, . . . , or $C_8$ may connect to any one or more of the detector units $p_1$, $p_2$, $p_3$, . . . , or $p_8$ In this way, the single event signal $S_k$ acquired by each detector unit $p_K$ may be transmitted to all of the coincidence logic circuits that may be related to $p_K$ through a data bus. The plurality of coincidence logic circuits may synchronically generate the coincidence counts of the plurality of detector units. FIG. 7 is a schematic diagram of an exemplary distribution of coincidence logic circuits according to some embodiments of the present disclosure. As shown in FIG. 7, the coincidence logic circuit $C_1$ may receive a single event signal $S_1$, $S_2$, . . . , $S_8$. The coincidence logic circuit $C_2$ may receive a single event signal $S_2$, $S_3$, . . . , $S_8$. The coincidence logic circuit $C_3$ may receive a single event signal $S_3$, $S_4$, . . . , $S_8$, . . . . The coincidence logic circuit $C_8$ may receive two single event signals $S_8$.

The plurality of coincidence logic circuits 62, connected to one or more corresponding detector units 61, may be configured to count the coincidence events. The coincidence events may include coincidence events acquired by a single detector unit 61 or two detector units 61 in accordance with a pairing rule. For example, in FIG. 6, two different single event signals $S_{11}$ and $S_{12}$ may be derived from two opposite detector components of the detector unit $p_1$, respectively. In some embodiments, two single event counts that meet the pairing rule may be from different detector units 61. For example, in FIG. 6, two different single event signals $S_{13}$ and $S_{21}$ are from two opposite detecting components in a slant which are on the detector unit $p_1$ and detector unit $p_2$, respectively. Here, which $p_k$ the two single events may be from may be determined based on the coincidence counts. An entire set of coincidence counts of the system P is represented by $c_{(k1, k2)}$, wherein k1,2=1,2, . . . , 8, k1 and k2 reflects a coincidence pairing relation of detector units 61.

For the PET system which has been expanded along the axial direction, whether the PET system has high sensitivity performance may mainly depend on whether the PET system may effectively acquire coincidence counts $C_{(k1, k2)}$, wherein k1≠k2. The existing electronic logic may not transmit all of the $S_k$ to a coincidence logic circuit to generate a coincidence count $c_{(k1, k2)}$, because the front-end electronics may get a dead-time effect and be palsied because of a high single event counting rate. Therefore, the general PET system may not work in normal clinical scanning. In some embodiments of the present disclosure, a plurality of coincidence logic circuits 62 may synchronically receive single event data of the detector units 61 and synchronically generate a plurality of coincidence counts of the detector units 61. Therefore, the problem of receiving and measuring massive coincidence signals may be solved.

Figure 8:
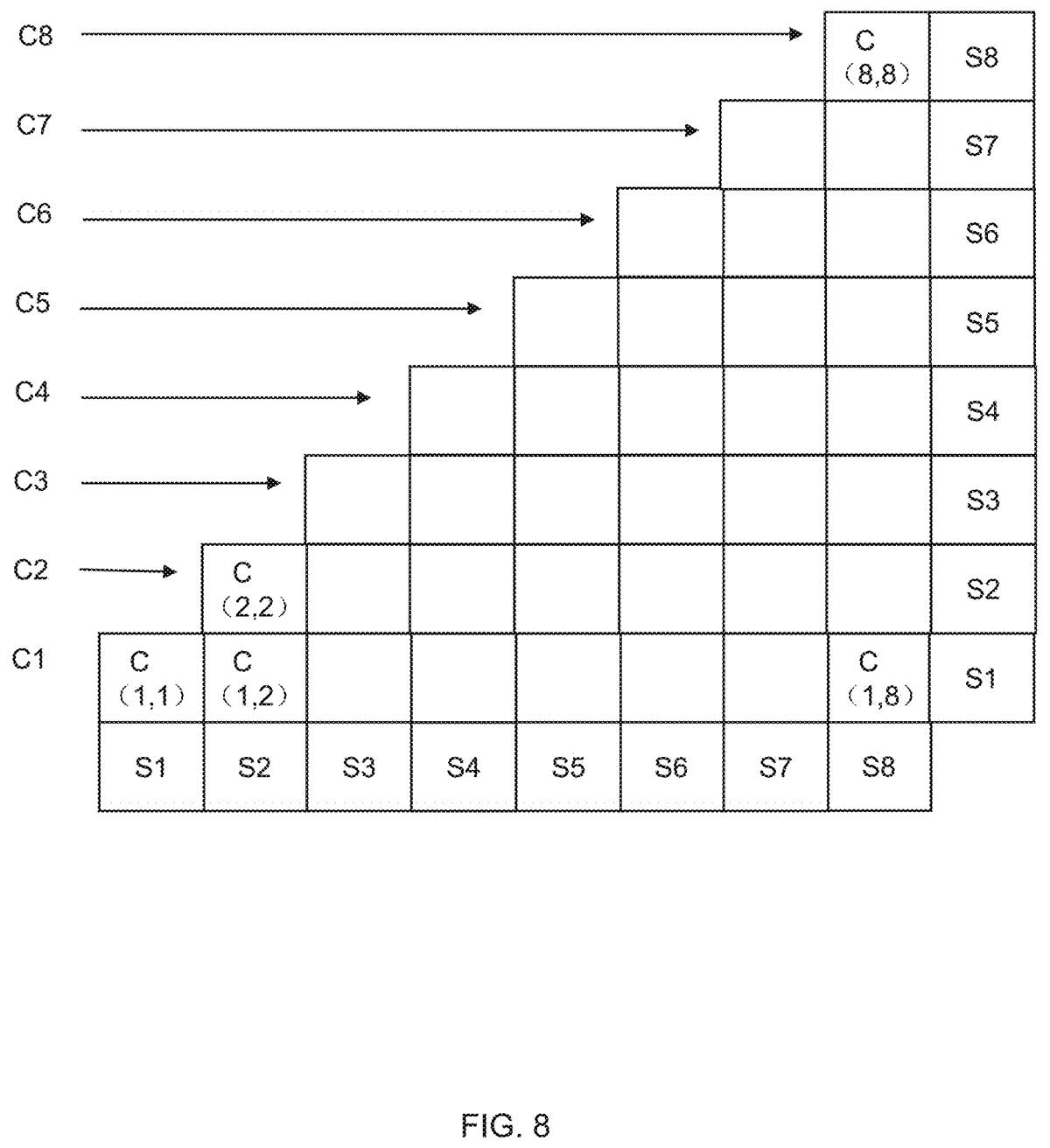

FIG. 8 is a schematic diagram of an exemplary assignment of a coincidence logic task according to some embodiments of the present disclosure. Each of coincidence logic circuits may count the coincidence events in a manner shown in FIG. 8. Coincidence events to be counted may include the coincidence events acquired by a single detector unit 61 or two detector units 61 in accordance with the pairing rule. For example, the pairing rule may refer to numbering the plurality of detector units in a sequential order, wherein the Nth detector unit may only match a detector unit associated with a number that is subsequent to N, wherein N is less than K, wherein K is the total number of the detector units, and wherein N and K are natural numbers.

Figure 9:
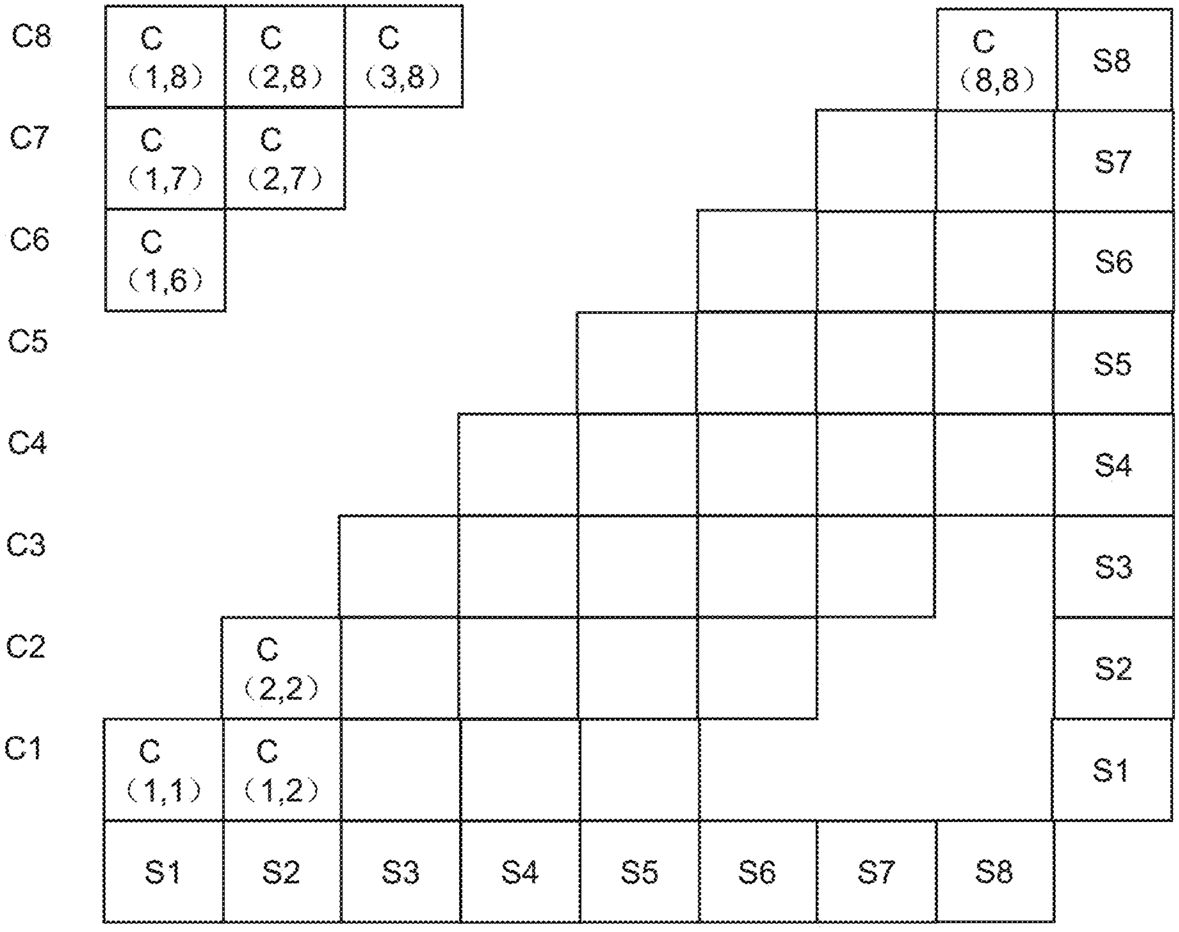
FIG. 9 is another schematic diagram of an exemplary assignment of a coincidence logic task according to some embodiments of the present disclosure.

In accordance with the pairing rule, the coincidence logic circuit C1 may be configured to: perform a coincidence count for two single events from the same detector unit p1; perform a coincidence count for two single events that are from the detector unit p1 and the detector unit p2, respectively; perform a coincidence count for two single events that are from the detector unit p1 and the detector unit p3, respectively; perform a coincidence count for two single events that are from the detector unit p1 and the detector unit p4, respectively; perform a coincidence count for two single events that are from the detector unit p1 and the detector unit p5, respectively; perform a coincidence count for two single events that are from the detector unit p1 and the detector unit p6, respectively; perform a coincidence count for two single events that are from the detector unit p1 and the detector unit p7, respectively; perform a coincidence count for two single events that are from the detector unit p1 and the detector unit p8, respectively; and generate coincidence counts $c_{(1, 1)}$, $c_{(1, 2)}$, $c_{(1, 3)}$, $c_{(1, 4)}$, $c_{(1, 5)}$, $c_{(1, 6)}$, $c_{(1, 7)}$, and $c_{(1, 8)}$. The coincidence logic circuit C2 may be configured to: perform a coincidence count for two single events from the same detector unit p2; perform a coincidence count for two single events that are from the detector unit p2 and the detector unit p3, respectively; perform a coincidence count for two single events that are from the detector unit p2 and the detector unit p4, respectively; perform a coincidence count for two single events that are from the detector unit p2 and the detector unit p5, respectively; perform a coincidence count for two single events that are from the detector unit p2 and the detector unit p6, respectively; perform a coincidence count for two single events that are from the detector unit p2 and the detector unit p7, respectively; perform a coincidence count for two single events that are from the detector unit p2 and the detector unit p8, respectively; and generate coincidence counts $c_{(2, 2)}$, $c_{(2, 3)}$, $c_{(2, 4)}$, $c_{(2, 5)}$, $c_{(2, 6)}$, $c_{(2, 7)}$, and $c_{(2, 8)}$. Similarly, the coincidence logic circuit C3 may be configured to generate coincidence counts $c_{(3, 3)}$, $c_{(3, 4)}$, . . . , $c_{(3, 8)}$; . . . , the coincidence logic circuit C8 may be configured to generate a coincidence count $c_{(8, 8)}$. In other words, according to a tag of the single event signal $S_k$, each $S_k$ may only do coincidence with $S_k$ that is generated by $p_k$ or $S_{k+1}$ that is generated by $p_{k+i}$. Therefore, the coincidence counts of the system P may be classified according to the two $p_k$ from which the single events are derived. $c_{(1,1)}$, $c_{(2, 2)}$, . . . , $c_{(8, 8)}$ are the coincidence counts detected by the single PET detector unit $p_k$, while other $c_{(k1, k2)}$, wherein k1≠k2, are the coincidence counts between the single event signal $S_{k1}$ generated by the detector unit $p_{k1}$ and the single event signal $S_{k2}$ generated by the detector unit $p_{k2}$. For the system P with K=8 detector units, as assignments of the coincidence logic task shown in FIG. 8, 8 detector units may have a total of K(K+1)/2=36 detector pairs, and each detector pair may include one or two detector units. In the 36 detector pairs, 8 detector pairs are from the same detector unit, and K(K=1)/2=28 detector pairs are from different detector units. The plurality of coincidence logic circuits may be configured to count the coincidence events obtained by the 36 detector pairs. In some embodiments, part of the detector pairs may be selected from the 36 detector pairs, for example, fewer than K(K+1)/2=36 detector pairs. The plurality of coincidence logic circuits may count the coincidence events obtained by the selected detector pairs. In some embodiments, as illustrated in FIG. 8, the single event counts generated by each of the detector units may be unevenly assigned to each of the coincidence logic circuits for coincidence counting. The numbers of the coincidence counts relating to $C_1$ through $C_8$ are 8, 7, and, . . . , 1. FIG. 9 is another schematic diagram of an exemplary assignment of a coincidence logic task according to some embodiments of the present disclosure. As shown in FIG. 9, the coincidence pairing task generated by each of detector units may be basically evenly assigned to the coincidence logic circuits. The numbers of the coincidence counts relating to $C_1$ through $C_8$ are 5, 5, 5, 5, 4, 4, and 4.

Figure 10:
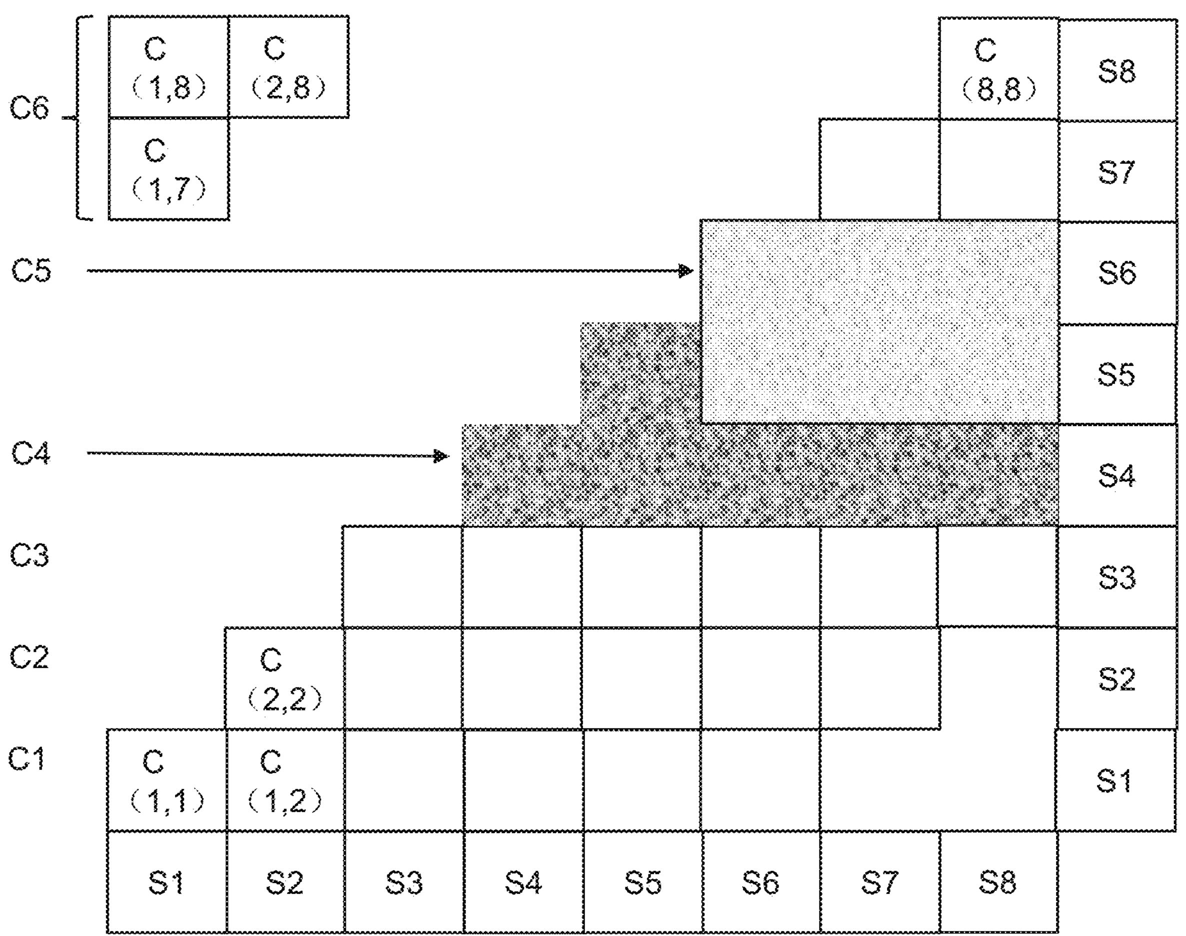
FIG. 10 is another schematic diagram of an exemplary distribution of a coincidence logic circuit and assignment of a coincidence pairing task according to some embodiments of the present disclosure.

FIG. 10 is another schematic diagram of an exemplary distribution of a coincidence logic circuit and assignment of coincidence pairing task according to some embodiments of the present disclosure. As shown in FIG. 10, the coincidence logic circuit may not be independently configured on each of the detector units. That is, there is no one-to-one correspondence between the detector units and the coincidence logic circuits. The coincidence pairing task from each of the detector units may be basically evenly assigned to the coincidence logic circuits. The numbers of the coincidence counts relating to the coincidence logic circuits $C_1$ through $C_6$ are 6. The coincidence counts $c_{(4, 4)}$, $c_{(4, 5)}$, $c_{(4, 6)}$, $c_{(4, 7)}$, $c_{(4, 8)}$, and $c_{(5, 5)}$ are assigned to the coincidence logic circuit $C_4$. The coincidence counts $c_{(5, 6)}$, $c_{(5, 7)}$, $c_{(5, 8)}$, $c_{(6, 6)}$, $c_{(6, 7)}$, and $c_{(6, 8)}$ are assigned to the coincidence logic circuit $C_5$. The coincidence counts $c_{(1, 7)}$, $c_{(7, 7)}$, $c_{(7, 8)}$, $c_{(1, 8)}$, $c_{(2, 8)}$, and $c_{(8, 8)}$, are assigned to the coincidence logic circuit $C_6$.

In another aspect of the present disclosure, a method for image reconstruction in the PET system is provided. The method may include: generating, by each of a plurality of detector units arranged along an axial direction, a plurality of single event counts; transmitting single event data generated by each of the detector units to one or more coincidence logic circuits, wherein the plurality of coincidence logic circuits are connected to one or more detector units; and synchronically generating coincidence counts relating to the one or more detector units.

Figure 11:
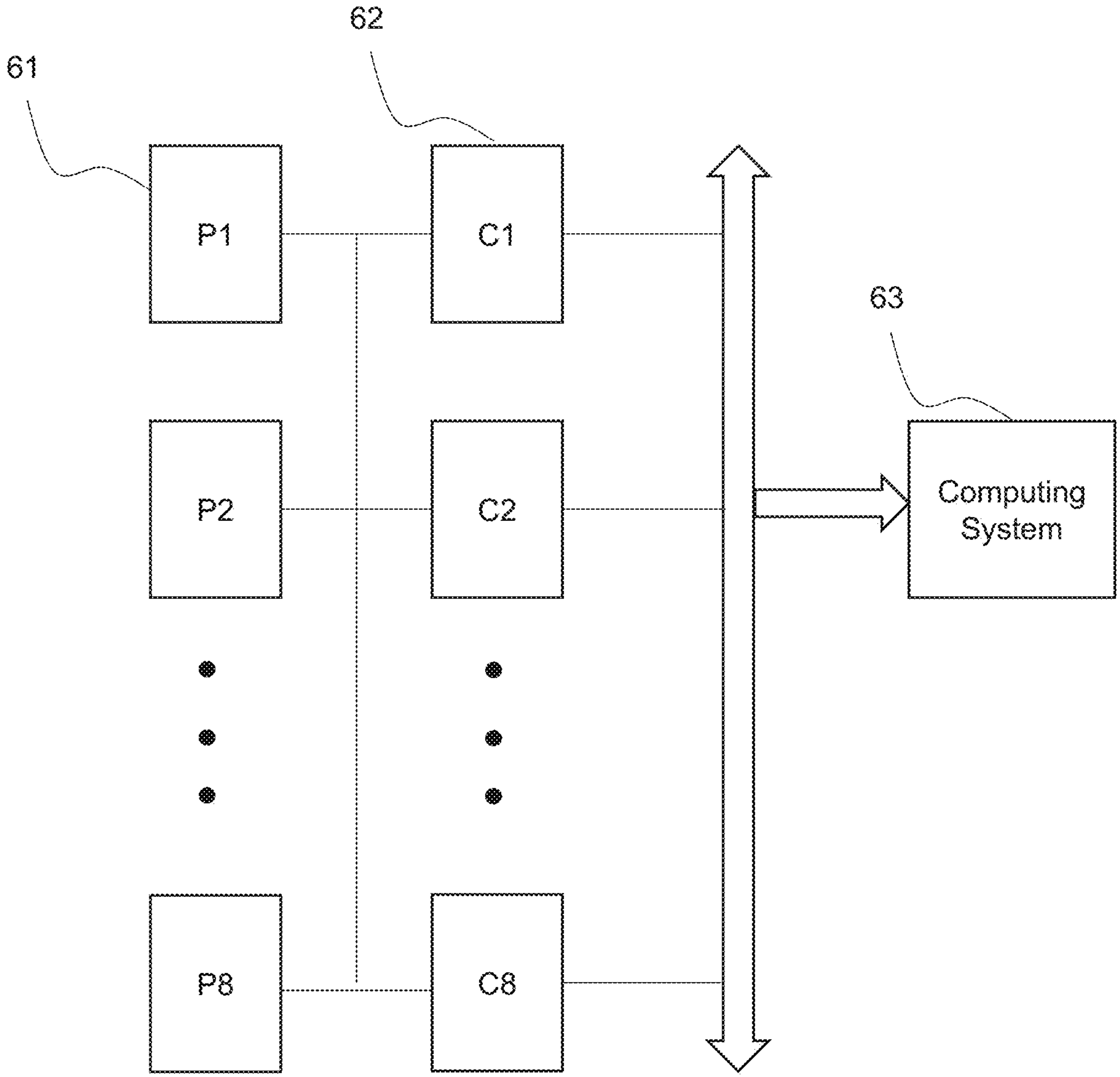
FIG. 11 is a block diagram of an exemplary image reconstruction architecture of the PET system according to some embodiments of the present disclosure.

FIG. 11 is a block diagram of an exemplary image reconstruction architecture of the PET system according to some embodiments of the present disclosure. As shown in FIG. 11, the image reconstruction architecture may include a plurality of detector units 61, a plurality of coincidence logic circuits 62, and a computing system 63. The details of the plurality of detector units 61 and the plurality of coincidence logic circuits 62 are discussed with reference to the above description, and are not repeated herein. The computing system 63 may be connected to the plurality of coincidence logic circuits 62. The computing system 63 may determine a direction of backward projection according to k1 and k2 of the coincidence count $c_{(k1, k2)}$ received from the system, and perform iterative reconstruction by performing forward projection and backward projection on images, for example, using the technique of Ordered Subsets Expectation Maximization (OSEM), to complete the image reconstruction. The computing system 63 may include a processor for backward projection calculation. The processor may be a general-purpose central processing unit (CPU) or a graphics processing unit (GPU).

Figure 12:
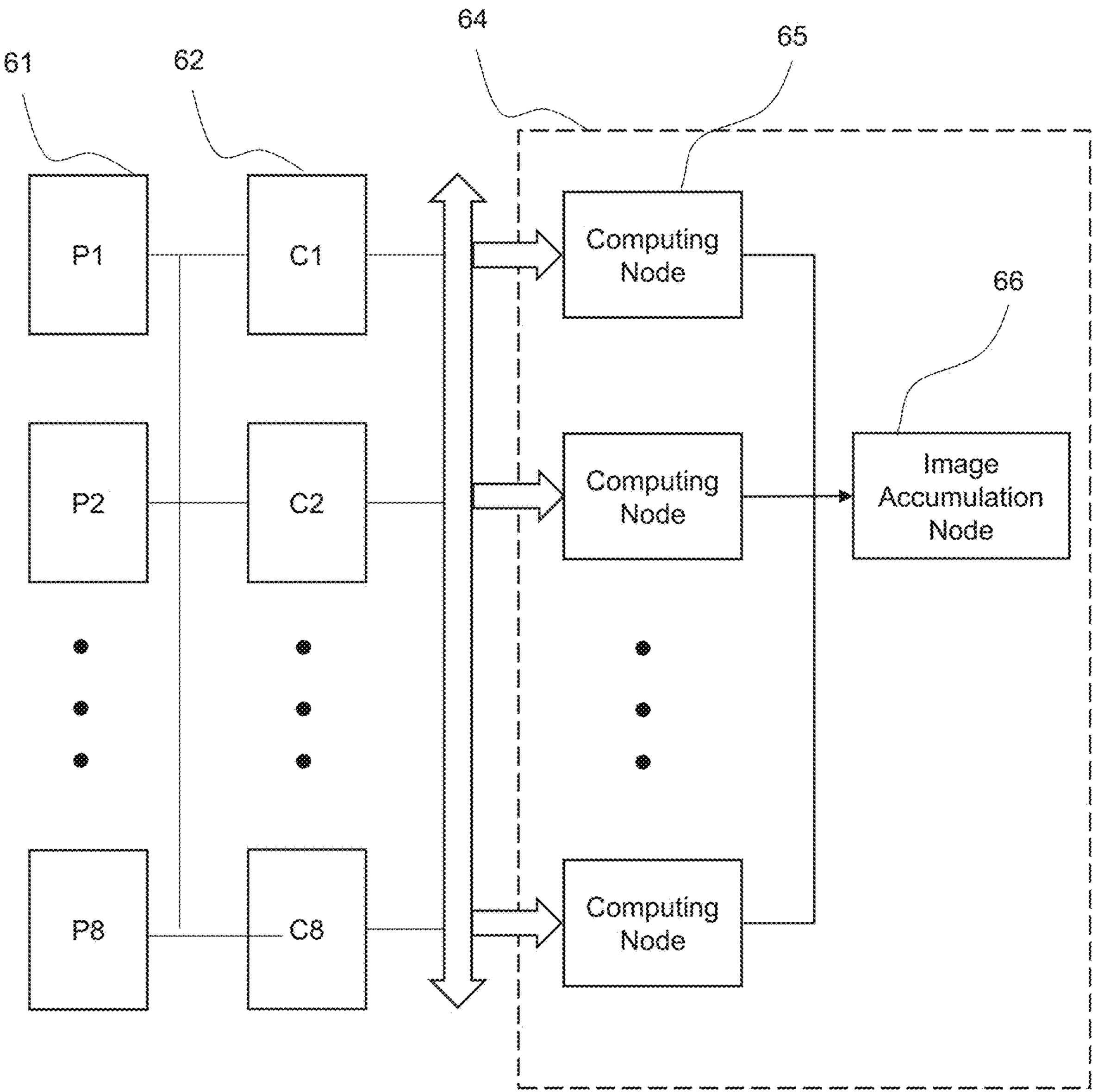
FIG. 12 is another block diagram of an exemplary image reconstruction architecture of the PET system according to some embodiments of the present disclosure.

FIG. 12 is another block diagram of an exemplary image reconstruction architecture of the PET system according to some embodiments of the present disclosure. As shown in FIG. 11 the image reconstruction architecture may include a plurality of detector units 61, a plurality of coincidence logic circuits 62, and a computing system 64. The details of the plurality of detector units 61 and the plurality of coincidence logic circuits 62 are discussed with reference to the above description, and are not repeated herein. The computing system 64 may include a plurality of computing nodes 65, each of which may correspondingly connect to each of the coincidence logic circuits 62. Each of computing nodes 65 may synchronically determine the direction of the forward and backward projection according to k1 and k2 of the coincidence event $c_{(k1, k2)}$ received from the system. Then a backward projection image may be generated by using the OSEM technique. Taking into account an efficiency of computing tasks, the coincidence events may be assigned randomly to each of computing nodes 65. Then the backward projection images may be transmitted to the image accumulation node 66 to be accumulated. When the accumulation is completed, an iteration may be completed for the image. The accumulated image may undergo the next forward projection. After several iterations, the image reconstruction may be completed. In some embodiments, an instance of the computing node is a first processor, and an instance of the image accumulation node is a second processor. The processor may be a general-purpose central processing unit (CPU) or a graphics processing unit (GPU).

In the embodiments of the present disclosure described above, the problems of expanding the axial scanning FOV, the high counting rate of the PET detector unit, and the receiving of massive coincidence signals may be solved by using one or more distributed coincidence logic circuits. The PET system with expanded axial scanning FOV may achieve high sensitivity performance. In addition, in the embodiments of the present disclosure described above, the system solves the problem of the rapid reconstruction of the massive coincidence signals, so that the PET system with the expanded axial scanning FOV may have the capability of instant and high-definition imaging for a full body.

Though the present disclosure includes some embodiments, it may be rather apparent to those skilled in the art that the above embodiments is intended to be presented by way of example only, and various alterations and modifications may occur without departing from the spirit of the present disclosure. These alterations and modifications to the embodiments within the spirit are intended to be suggested by the claims of the present disclosure.

What is claimed is:

1. A positron emission tomography (PET) system, comprising:

a plurality of detector units arranged along an axial direction, each detector unit of the plurality of detector units being configured to generate a plurality of single event counts;

a plurality of distributed coincidence logic circuits, each distributed coincidence logic circuit of the plurality of distributed coincidence logic circuits being operably connected to at least one of the plurality of detector units, wherein the plurality of single event counts generated by the each detector unit is transmitted, through a data bus, to all of the distributed coincidence logic circuits of the plurality of distributed coincidence logic circuits that are connected to the each detector unit, the each distributed coincidence logic circuit being configured to:

obtain the single event counts generated by the at least one of the plurality of detector units that is connected to the each distributed coincidence logic circuit; and generate one or more coincidence counts relating to the at least one of the plurality of detector units synchronically with the rest of the plurality of distributed coincidence logic circuits; and a computing system configured to reconstruct an image by performing, based on a plurality of coincidence counts generated by the plurality of distributed coincidence logic circuits, forward projection calculation and backward projection calculation.

2. The system of claim 1, wherein the computing system includes a plurality of computing nodes, and each of the plurality of computing nodes connects to one or more of the plurality of distributed coincidence logic circuits, and the plurality of computing nodes synchronically determine directions of forward projection and backward projection according to a coincidence pairing relation of the plurality of detector units.

3. The system of claim 1, wherein the plurality of detector units include a first detector unit and a second detector unit;

the first detector unit is spaced apart from the second detector by at least another detector unit of the plurality of detector units; and at least a portion of coincidence events corresponding to the plurality of coincidence counts include intra-unit coincidence events acquired by the first detector unit, and cross-unit coincidence events acquired by the first detector unit and the second detector unit.

4. The system of claim 1, wherein single event data generated by the plurality of detector units is unevenly distributed to the plurality of distributed coincidence logic circuits for coincidence counting.

5. The system of claim 1, wherein at least part of the plurality of distributed coincidence logic circuits perform coincidence counting for single event data from a unit single detector unit.

6. The system of claim 1, wherein a count of the plurality of distributed coincidence logic circuits is equal to a count of the plurality of detector units in the PET system.

7. The system of claim 6, wherein each of the plurality of distributed coincidence logic circuits is provided on a corresponding detector unit.

8. The system of claim 1, wherein a count of the plurality of distributed coincidence logic circuits is smaller than a count of the plurality of detector units in the PET system.

9. The system of claim 1, wherein the computing system includes a first processor connected to the plurality of distributed coincidence logic circuits;

the one or more coincidence counts generated by the each distributed coincidence logic circuit are transmitted to the first processor;

the first processor performs backward projection of the one or more coincidence counts; and the computing system performs forward projection based on the backward projection.

10. The system of claim 1, wherein:

the computing system includes a plurality of first processors;

each of the first processors is connected to one or more of the plurality of distributed coincidence logic circuits;

the one or more coincidence counts generated by the each distributed coincidence logic circuit are transmitted to each of the plurality of first processors; and the plurality of first processors synchronically perform backward projection of the plurality of coincidence counts.

11. The system of claim 10, wherein the one or more coincidence counts generated by the each distributed coincidence logic circuit is transmitted to the each of the plurality of first processors randomly.

12. The system of claim 10, wherein:

the computing system further includes a second processor;

the second processor is connected to the plurality of first processors;

a result of backward projection generated by each of the plurality of first processors is transmitted to the second processor;

the second processor superimposes the results of backward projection; and the computing system performs forward projection based on the superimposed result of backward projection.

13. The system of claim 3, wherein the first detector unit matches with the second detector unit according with a pairing rule, the pairing rule comprising:

numbering the plurality of detector units in a sequential order, wherein the Nth detector unit only matches a detector unit associated with a number that is subsequent to N, wherein N is less than K, wherein Kis the total number of the detector units, and wherein N and K are natural numbers.

14. The system of claim 1, wherein the computing system includes a plurality of computing nodes, and each of the plurality of computing nodes connects to a portion of the plurality of coincidence logic circuits.

15. The system of claim 1, wherein the plurality of detector units are numbered in a sequential order;

one of the plurality of coincidence logic circuits is configured to only perform a coincidence count for two single events from an Nth detector unit of the plurality of detector units and a coincidence count for two single events that are from the Nth detector unit and one of the plurality of detector units that is with a number subsequent to N;

N is less than a total number of the plurality of detector units.

16. The system of claim 2, wherein the computing system includes an image accumulation node connected with the plurality of computing nodes, the plurality of computing nodes synchronically generate a plurality of backward projection images by using an Ordered Subsets Expectation Maximization (OSEM) technique, the plurality of backward projection images are transmitted to the image accumulation node to be accumulated, and the backward projection images which are accumulated undergo a next forward projection.

17. The system of claim 1, wherein each of at least one of the plurality of distributed coincidence logic circuits is connected to at least three detector units of the plurality of detector units.

18. A method for image reconstruction in a PET system, comprising:

generating, by each detector unit of a plurality of detector units arranged along an axial direction, a plurality of single event counts;

transmitting single event data generated by the each detector unit to one or more of a plurality of coincidence logic circuits, wherein each of the plurality of coincidence logic circuits is operably connected to one or more of the plurality of detector units;

generating coincidence counts relating to the plurality of detector units synchronically with the rest of the plurality of coincidence logic circuits, wherein a single coincidence logic circuit of the plurality of coincidence logic circuits is configured to perform a coincidence count for two single events from the same detector unit, and perform a coincidence count for two single events that are from two different detector units respectively; and reconstructing an image by performing, based on the coincidence counts, forward projection calculation and backward projection calculation.

19. The method of claim 18, wherein the reconstructing an image comprising:

determining a direction of backward projection according to a coincidence pairing relation of one or more detector units relating to each of the coincidence counts; and performing the forward projection calculation and the backward projection calculation based on the direction.

20. A non-transitory computer readable medium storing instructions, the instructions, when executed by at least one processor, causing the at least one processor to implement a method for image reconstruction in a positron emission tomography (PET) system comprising:

generating, by each detector unit of a plurality of detector units arranged along an axial direction, a plurality of single event counts;

transmitting single event data generated by the each detector unit to one or more of a plurality of coincidence logic circuits, wherein each of the plurality of coincidence logic circuits is operably connected to one or more of the plurality of detector units;

for each of the plurality of coincidence logic circuits, generating, by the coincidence logic circuit, one or more coincidence counts relating to the one or more of the plurality of detector units synchronically with the rest of the plurality of coincidence logic circuits, wherein a single coincidence logic circuit of the plurality of coincidence logic circuits is configured to perform a coincidence count for two single events from the same detector unit and perform a coincidence count for two single events that are from two non-adjacent detector units respectively, and the two non-adjacent detector units refer to two of the plurality of detector units that are separated, along the axial direction, by at least one other detector unit of the plurality of detector units; and reconstructing an image by performing, based on the coincidence counts, forward projection calculation and backward projection calculation.

* * * * *